(12) United States Patent
Dextradeur et al.

(10) Patent No.: US 7,699,800 B2
(45) Date of Patent: *Apr. 20, 2010

(54) MULTI-CATHETER INSERTION DEVICE AND METHOD

(75) Inventors: Alan J. Dextradeur, Franklin, MA (US); Gary Magram, Fairfax, VA (US)

(73) Assignee: Codman & Shurtleff, Inc., Raynham, MA (US)

( * ) Notice: Subject to any disclaimer, the term of this patent is extended or adjusted under 35 U.S.C. 154(b) by 680 days.

This patent is subject to a terminal disclaimer.

(21) Appl. No.: 11/081,577

(22) Filed: Mar. 16, 2005

(65) Prior Publication Data

US 2005/0159697 A1    Jul. 21, 2005

Related U.S. Application Data

(63) Continuation of application No. 10/047,204, filed on Jan. 14, 2002, now Pat. No. 6,913,589.

(51) Int. Cl.
*A61M 37/00* (2006.01)

(52) U.S. Cl. .............................. 604/8; 604/9; 604/4.01; 604/5.01; 604/6.1

(58) Field of Classification Search ............... 604/7–10, 604/264, 508, 510, 164.01, 108, 164.13, 604/170.02, 6.16, 533, 534, 284; 606/153
See application file for complete search history.

(56) References Cited

U.S. PATENT DOCUMENTS

| 3,144,868 A | 8/1964 | Jascalevich |
| 3,867,937 A | 2/1975 | Schwartz |
| 3,867,945 A | 2/1975 | Long |
| 4,072,153 A | 2/1978 | Swartz |
| 4,182,343 A | 1/1980 | Inaba |

(Continued)

FOREIGN PATENT DOCUMENTS

JP    58049158    3/1983

(Continued)

OTHER PUBLICATIONS

Phoenix Anti-Blok "*Catheter-Reservoir*" (*For CSF Shunting*); Internet Site Address: http://www.shunt.com/biomedical/instructions/NS/AntiBlokCR.htm Aug. 2005.

*Primary Examiner*—Leslie R Deak
(74) *Attorney, Agent, or Firm*—Nutter McClemen & Fish LLP (57) ABSTRACT

An implantable shunt device having a primary catheter and at least two secondary catheters extending from the primary catheter is provided. The primary catheter includes a connecting end, an open end, and an inner lumen extending therebetween. Each of the secondary catheters extend from the connecting end of the primary catheter and include a fluid passageway formed therein in fluid communication with the inner lumen of the primary catheter. Each secondary catheter also includes at least one fluid entry port in fluid communication with the fluid passageway. In an exemplary embodiment, the fluid entry ports are disposed on an inwardly facing portion of each of the secondary catheters. The shunt device can be used for a variety of diagnostic and therapeutic procedures, including for the removal or introduction of fluid to a treatment site.

12 Claims, 7 Drawing Sheets

U.S. PATENT DOCUMENTS

| | | |
|---|---|---|
| 4,215,695 A | 8/1980 | Spitz et al. |
| 4,377,169 A | 3/1983 | Banks |
| 4,406,656 A * | 9/1983 | Hattler et al. ............... 604/523 |
| 4,432,853 A * | 2/1984 | Banks .................. 204/192.34 |
| 4,578,057 A | 3/1986 | Sussman |
| 4,655,745 A | 4/1987 | Corbett |
| 4,692,155 A | 9/1987 | Zimmer |
| 4,767,400 A | 8/1988 | Miller et al. |
| 4,784,638 A | 11/1988 | Ghajar et al. |
| 4,925,452 A * | 5/1990 | Melinyshyn et al. ........ 604/284 |
| 4,950,224 A * | 8/1990 | Gorsuch et al. ............ 604/6.04 |
| 4,950,232 A | 8/1990 | Ruzicka et al. |
| 5,098,411 A | 3/1992 | Watson et al. |
| 5,405,316 A | 4/1995 | Magram |
| 5,531,673 A | 7/1996 | Helenowski |
| 5,891,111 A * | 4/1999 | Ismael ....................... 604/541 |
| 5,897,528 A | 4/1999 | Schultz |
| 5,913,852 A | 6/1999 | Magram |
| 6,013,051 A | 1/2000 | Nelson |
| 6,030,358 A | 2/2000 | Odland |
| 6,254,610 B1 | 7/2001 | Darvish et al. |
| 6,616,652 B1 * | 9/2003 | Harper et al. ............ 604/892.1 |
| 6,814,718 B2 * | 11/2004 | McGuckin, Jr. et al. ..... 604/264 |
| 6,913,589 B2 * | 7/2005 | Dextradeur et al. ............ 604/8 |
| 7,037,288 B2 * | 5/2006 | Rosenberg et al. ............. 604/8 |

FOREIGN PATENT DOCUMENTS

| | | |
|---|---|---|
| JP | 10179927 | 7/1998 |
| JP | 2000300679 | 10/2000 |
| WO | WO 89/02290 | 3/1989 |
| WO | 9105575 | 5/1991 |
| WO | WO 98/11934 | 3/1998 |

* cited by examiner

MULTI-CATHETER INSERTION DEVICE AND METHOD

CROSS-REFERENCE TO RELATED APPLICATIONS

This APPLICATION is a continuation of application Ser. No. 10/047,204, filed Jan. 14, 2002, which is hereby incorporated by reference in its entirety.

FIELD OF THE INVENTION

The present invention relates to a catheter device and method useful with a shunt system, and in particular to a multi-catheter shunt device that minimizes the risk of blockage or obstruction or the catheter pores.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. First, because CSF keeps the brain and spinal cord buoyant, it acts as a protective cushion or "shock absorber" to prevent injuries to the central nervous system. Second, the fluid barrier between the CSF and the blood prevents harmful substances from flowing from the capillaries into the CSF.

Hydrocephalus, which can affect people of any age, but affects mostly infants and young children, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF requires an increasing pressure for CSF to be absorbed into the bloodstream. This increasing pressure can interfere with the perfusion of the nervous system.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the pores. The pores of the ventricular catheter can also be obstructed by debris, bacteria, or blood clogged in the pores of the catheter. Additionally, problems with the ventricular catheter can arise from overdrainage of the CSF, which can cause the ventricle walls to collapse upon the catheter and block the pores in the catheter wall, thereby preventing CSF drainage.

Some of these problems can be treated by backflushing, which is a process that uses the CSF present in the shunt system to remove the obstructing matter. This process can be ineffective, however, due to the small size of the pores of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the pores and the degree and extent to which the pores have been clogged.

Occluded ventricular catheters can also be repaired by cauterizing the catheter to reopen existing pores, or optionally to create additional pores. These repairs, however, may be incapable of removing obstructions from the ventricular catheter depending on the location of the clogged pores. Additionally, the extent of tissue growth into and around the catheter can also preclude the creation of additional pores, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by simply removing the obstructed catheter from the ventricle, the growth of the choroid plexus and other tissues around the catheter and into the pores can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt system that minimizes or eliminates the risk of blockage or obstruction of the catheter pores, and reduces the need for repeated repair and/or replacement.

SUMMARY OF THE INVENTION

The present invention provides an implantable shunt device having a primary catheter, e.g., an elongate trunk conduit, and multiple secondary catheters, e.g., branch conduits. The primary catheter includes a connecting end, an open end, and an inner lumen extending therebetween. Each of the secondary catheters extend from the connecting end of the primary catheter and include a fluid passageway formed therein in fluid communication with the inner lumen of the primary catheter. Each secondary catheter also includes at least one fluid entry port in fluid communication with the fluid passageway. In an exemplary embodiment, the fluid entry ports are disposed on an inwardly facing portion of each of the secondary catheters.

A variety of configurations are provided for mating the secondary catheters to the primary catheter. In one embodiment, for example, the secondary catheters each include a proximal end mated to the connecting end of the primary catheter, and a sealed distal end. In another embodiment, the connecting end of the primary catheter includes an end cap having several bores leading to the inner lumen of the primary catheter. Each bore is adapted to mate to or receive one of the secondary catheters. The end cap and the bores in the primary catheter are effective to form a seal between the fluid passageway formed in each of the secondary catheters and the inner lumen of the primary catheter. In another embodiment, the secondary catheters can be formed integrally with the primary catheter.

The shunt device can optionally include at least one support bracket disposed between each of-the-secondary catheters for securing the secondary catheters in a desired position relative to each other. For example, the support brackets can be adapted to position the secondary catheters at a predetermined distance apart from each other. This configuration is effective to prevent or reduce the risk of blockage of the fluid entry ports in the secondary catheters.

In others aspects, the shunt device can be adapted to receive a rigid stylet for implanting the shunt device at a treatment site. The connecting end of the primary catheter can include a self-sealing valve, e.g., a septum, adapted to receive a rigid stylet. The self-sealing valve is preferably disposed between the inner lumen of the primary catheter and a region external to the inner lumen of the primary catheter. Each support bracket can also include a central bore extending therethrough and adapted to receive the rigid stylet. In use, the rigid stylet is removably disposed through the inner lumen of the primary catheter, through the self-sealing valve in the connecting end of the primary catheter, between the plurality of secondary catheters, and through at least one of the support brackets. The shunt device can also optionally include a distal cap disposed around the distal end of each of the secondary catheters. The distal cap is effective to prevent a distal end of the rigid stylet from extending beyond the distal end of the device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
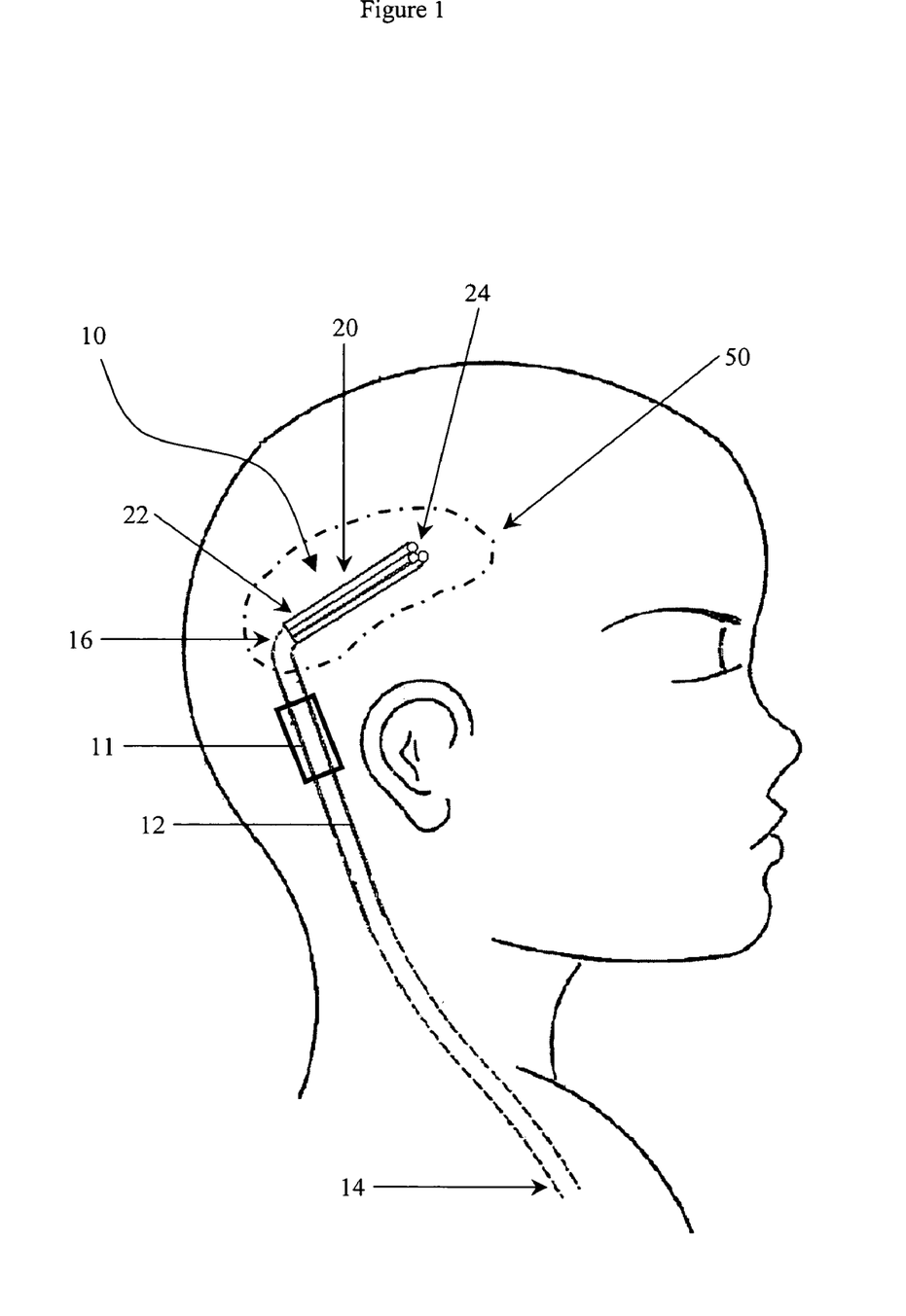
FIG. 1 is a perspective view, semi-transparent illustration of a portion of a shunt device implanted within a patient's cerebral ventricle according to the present invention.

As shown in FIG. 1, the present invention generally provides an implantable shunt device 10 including a primary catheter 12, or trunk conduit, having a first, open end 14, and a second, connecting end 16, and at least two secondary catheters 20, or branch conduits, extending from the connecting end 16 of the primary catheter 12. For illustration purposes, only three secondary catheters 20a, 20b, 20c are shown. However, a person having ordinary skill in the art will appreciate that the shunt device 10 can include two or more secondary catheters 20.

The shunt device 10 can be used for a variety of diagnostic and therapeutic procedures, including for the removal or introduction of fluid to a treatment site. In an exemplary embodiment, as shown in FIG. 1, the shunt device is used for treating hydrocephalus. The secondary catheters 20, and optionally at least a portion of the primary catheter 12, are implanted within one of the patient's cerebral ventricles, which contains cerebrospinal fluid (CSF). The shunt device 10 is effective to transport fluid from the ventricle, via the secondary catheters 20 and the primary catheter 12, to another location in the body where the CSF can be absorbed into the circulatory system.

Figure 2A:
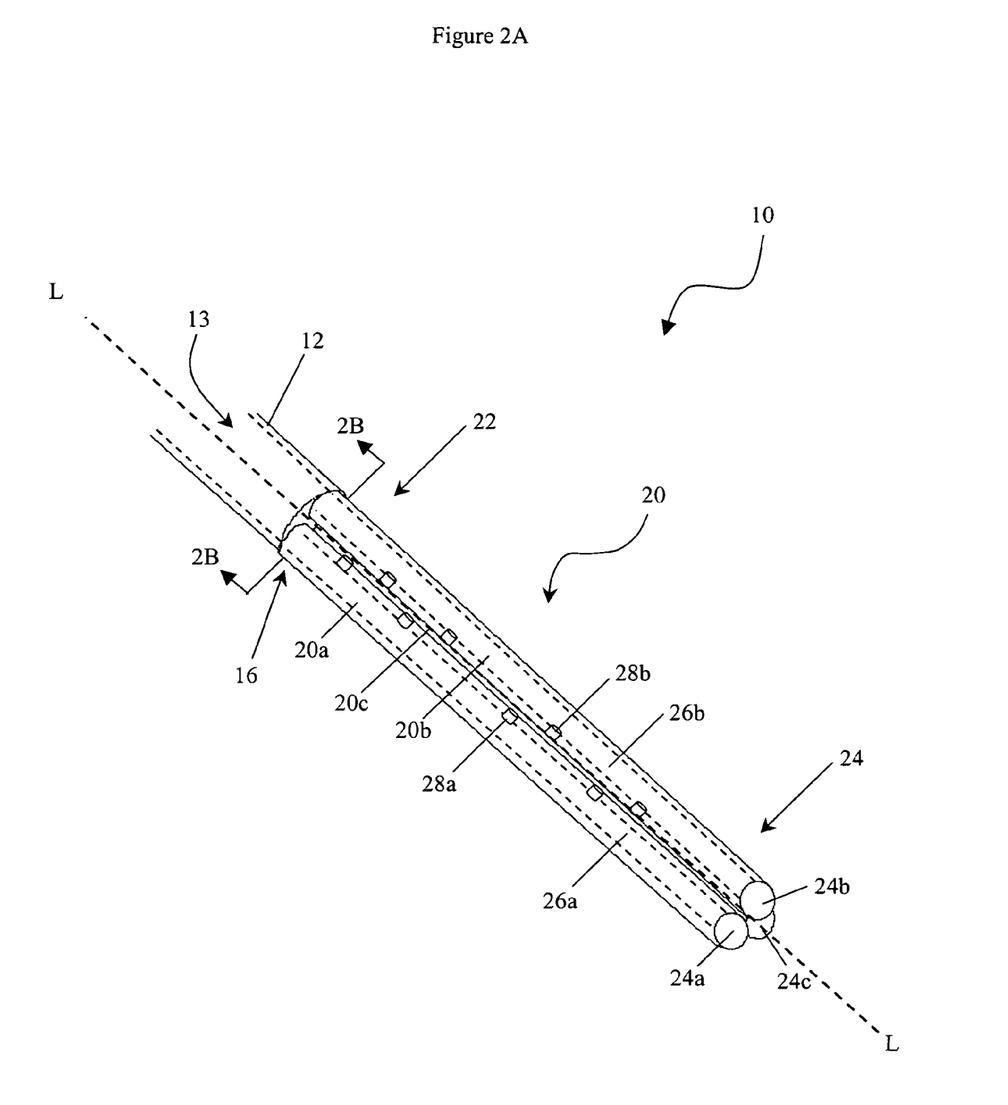
FIG. 2A is a perspective view of a portion of the shunt device of FIG. 1 having a primary catheter and several secondary catheters.

FIG. 2A illustrates a more detailed view of the shunt device 10. As shown, an inner lumen 13 extends between the first and second ends 14, 16 of the primary catheter 12. The inner lumen 13 is in fluid communication with a fluid passageway 26a, 26b formed in each of the secondary catheters 20a, 20b, 20c. At least one fluid entry port 28a, 28b, e.g., an inflow pore, extends through an outer wall of each of the secondary catheters 20a, 20b, 20c and into the fluid passageway 26a, 26b. In use, fluid can travel through the entry ports 28a, 28b into the fluid passageway 26a, 26b of each of the secondary catheters 20a, 20b, 20c, to the inner lumen 13 of the primary catheter 12 which will direct the fluid to another site in a patient's body. Conversely, fluid can also travel in the opposite direction.

Figure 2B:
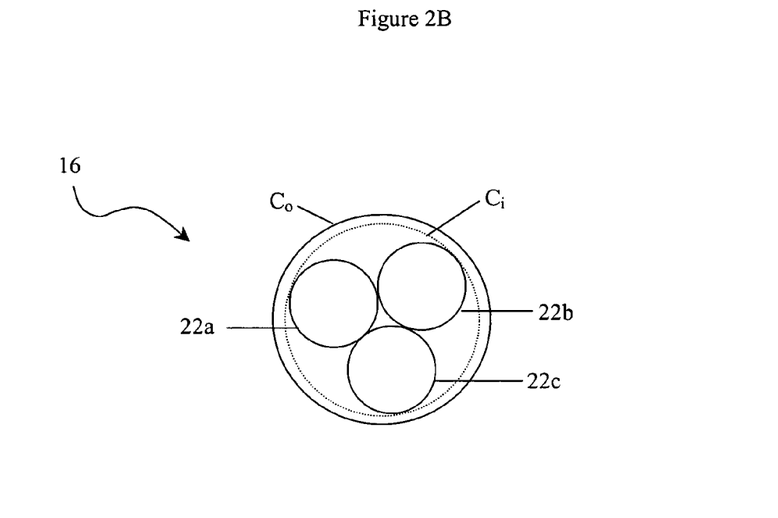
FIG. 2B is a cross-sectional view of the shunt device of FIG. 2A at lines 2B-2B.
Figure 2C:
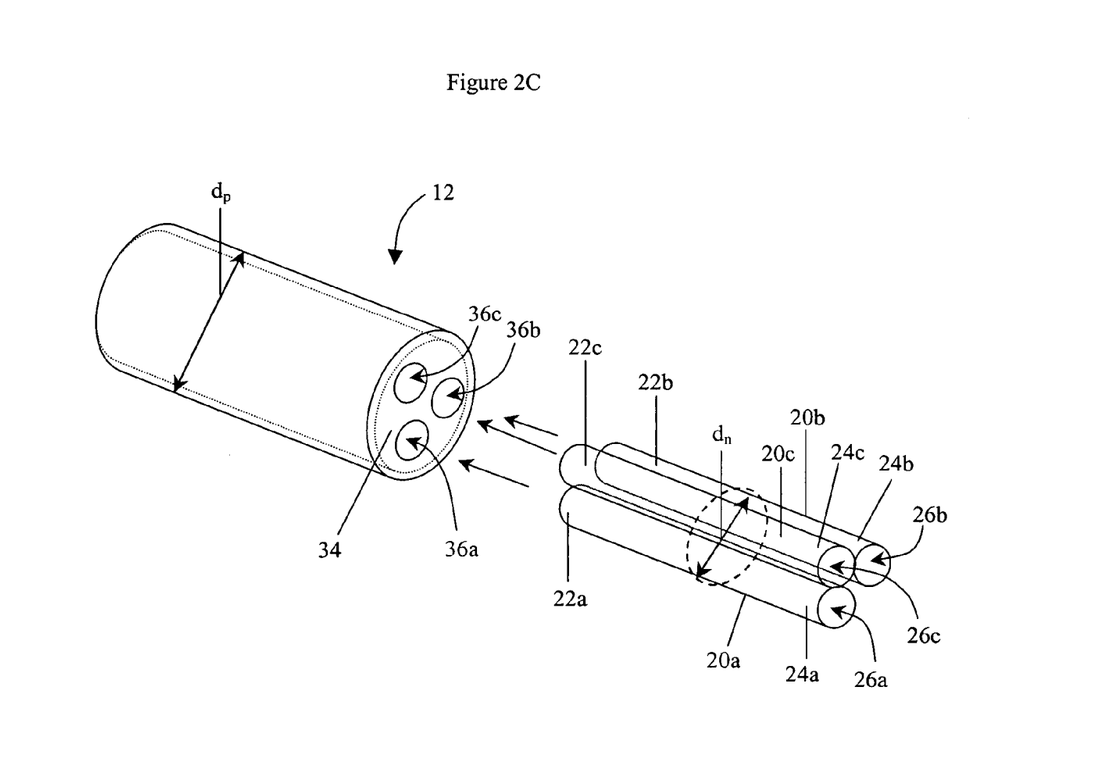
FIG. 2C is a perspective view of a disassembled shunt device according to another embodiment of the present invention.

The primary catheter 12, as shown in FIGS. 2A-2C, can have virtually any shape and size, but is preferably a substantially elongate cylindrical member having an inner lumen 13 extending therethrough. The open end 14 of the primary catheter 12 can be adapted for a variety of uses. By way of non-limiting example, the open end 14 of the primary catheter 12 can extend from the patient's body, can be implanted within the body, or can be mated to another medical device. In an exemplary embodiment, the open end 14 is either implanted at another location within the patient's body that is adapted to receive CSF fluid from the cerebral ventricle, or is mated to a shunt valve 11 (FIG. 1) which is mated to another catheter that extends to a site in the patient's body. The shunt valve is effective to regulate the flow of the CSF through the system.

The connecting end 16 of the primary catheter 12 mates to or receives the secondary catheters 20, and can have a variety of configurations. Preferably, the connecting end 16 of the primary catheter 12 forms a seal around a distal end 22 of each of the secondary catheters 20a, 20b, 20c to retain fluid within the inner lumen 13 of the primary catheter 12. As shown in FIGS. 2B and 2C, the connecting end 16 can include an end cap 34 having at least one bore 36 formed therein and extending into the inner lumen 13 of the primary catheter 12. Each bore 36a, 36b, 36c is sized to mate to or receive a distal end 22 of one of the secondary catheters 20a, 20b, 20c. As a result, the fluid passageway of each of the secondary catheters 20 is in fluid communication with the inner lumen 13 of the primary catheter 12. The end cap 34 can be formed integrally with the primary catheter 12, fixedly attached to the primary catheter 12, or it can be removably mated to the primary catheter. A variety of mating techniques can be used to connect the end cap 34 to the connecting end 16 of the primary catheter 12. By way of non-limiting example, the end cap 34 can be welded, ultrasonically bonded, adhesively attached, or mechanically mated to the primary catheter 12.

While the size and shape of the primary tubular catheter 12 can vary, the catheter preferably has an outer circumference $C_o$ in the range of about 2.5 mm to 3.0 mm, and more preferably about 2.7 mm. The inner circumference $C_i$ can also vary, but should have a size sufficient to permit fluid to flow therethrough. The inner circumference $C_i$ can be, for example, in the range of about 1 mm to 1.7 mm, and more preferably about 1.4 mm. The length of the primary tubular catheter 12 will vary depending on the intended use, but preferably the length is in the range of about 10 cm to 22 cm, and more preferably about 12 cm.

The secondary catheters 20, which extend from the connecting end 16 of the primary catheter 12, can also have any shape and size, but are preferably elongate cylindrical members. The shunt device 10 can include two or more secondary catheters 20, however, for illustration purposes, the shunt device 10 is shown having three secondary catheters 20a, 20b, 20c. Referring to FIGS. 2A-2C, the secondary catheters 20a, 20b, 20c each have a proximal end 22a, 22b, 22c, a distal end 24a, 24b, 24c, and a fluid passageway 26a, 26b, 26c extending therebetween. The fluid passageway 26a, 26b, 26c extends through the proximal end 22a, 22b, 22c of each of the secondary catheters 20a, 20b, 20c to allow fluid to flow therethrough, and terminates at a position proximal to the distal end 24a, 24b, 24c of each of the secondary catheters 20a, 20b, 20c. The distal ends 24a, 24b, 24c of the secondary catheters 20a, 20b, 20c can have a variety of configurations, but are preferably rounded to facilitate insertion of the shunt device 10 into a treatment site. Alternatively, the distal ends 24a, 24b, 24c can be open or include a fluid entry port to allow fluid to flow therethrough.

Figure 6:
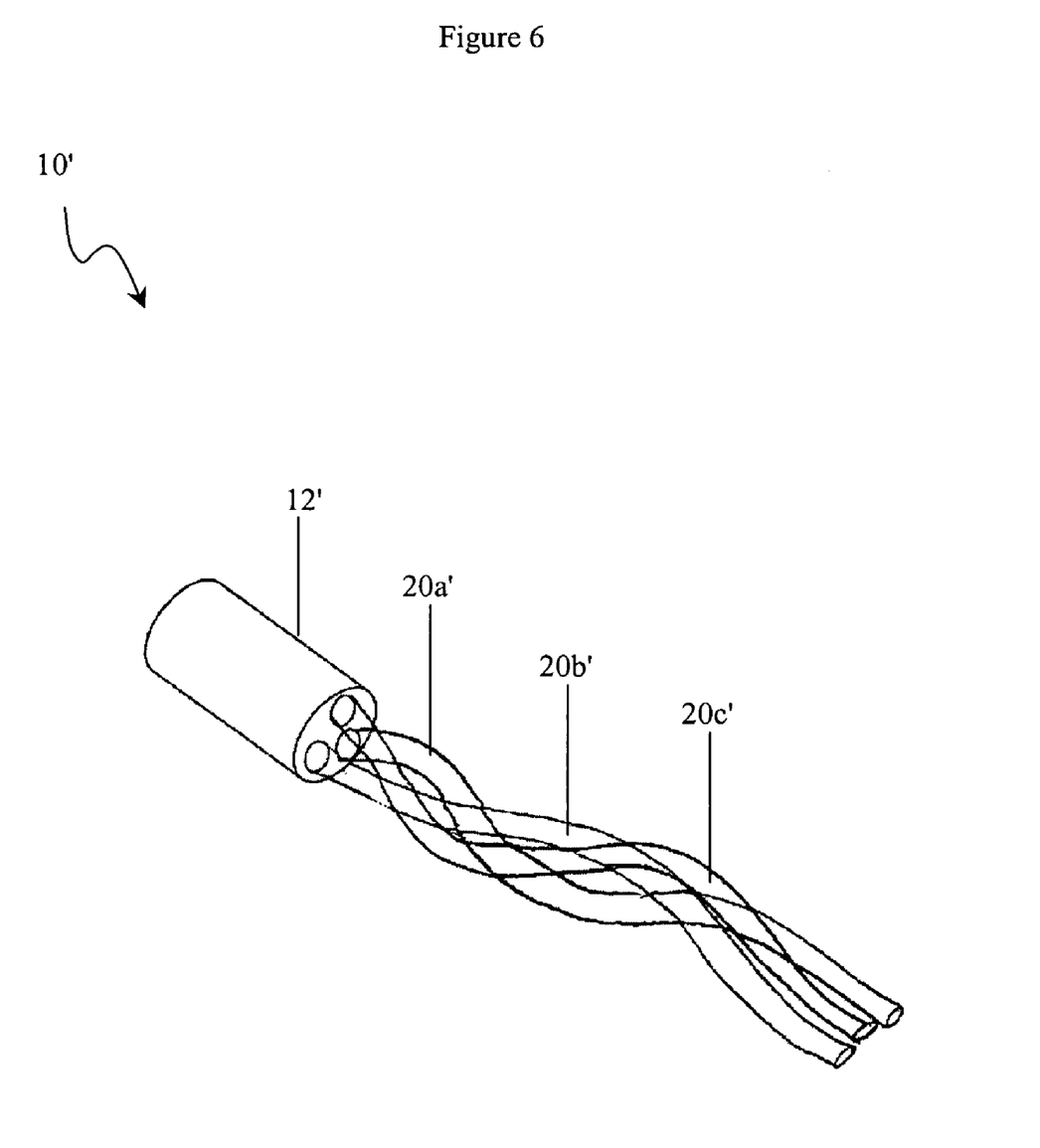
FIG. 6 is a perspective view of another embodiment of a shunt device according to the present invention.

A person having ordinary skill in the art will appreciate that the configuration of the secondary catheters can vary. By way of non-limiting example, each secondary catheter 20, or a portion of each secondary catheter, can have a helical shape. In such an embodiment, the fluid entry ports are preferably disposed on an inwardly facing surface of the helically shaped catheter. In a further embodiment, shown in FIG. 6, the secondary catheters 12a', 12b', 12c' can have a generally elongate shape, or alternatively they can have a helical shape (not shown), and can be intertwined, e.g., twisted, braided, or weaved together, to have a combined substantially cylindrical shape to facilitate insertion of the shunt device 10' into a treatment site. The secondary catheters can be intertwined as an alternative to using support brackets, or optionally in addition to using support brackets. In an exemplary embodiment, the secondary catheters are intertwined by rotating the catheters about 360° along the central longitudinal axis L of the instrument.

The proximal end 22a, 22b, 22c of each of the secondary catheters 20a, 20b, 20c is mated to or extends into the bores 36a, 36b, 26c in the end cap 34 of the primary catheter 12. In one embodiment (not shown), a proximal portion of each secondary catheter 20a, 20b, 20c extends through the bore 36a, 36b, 36c in the end cap 34 and into the inner lumen 13 of the primary catheter 12. Alternatively, the secondary catheters 20a, 20b, 20c can extend into the bores 36a, 36b, 36c in the end cap 34 and entirely through the primary catheter 12 such that the proximal ends 22a, 22b, 22c extend out the open end 14 of the primary catheter 12. This configuration would allow the position of the secondary catheters 20a, 20b, 20c with respect to the primary catheter 12 to be controlled. For example, the proximal ends 22a, 22b, 22c could be grasped and moved in a proximal or distal direction to cause the distal ends 24a, 24b, 24c of the secondary catheters 20a, 20b, 20c to move between a position in which the secondary catheters 20a, 20b, 20c are substantially disposed within the primary member 12 and a position in which the secondary catheters 20a, 20b, 20c extend outward from the connecting end 16 of the primary catheter 12.

In an exemplary embodiment, the proximal ends 22a, 22b, 22c of the secondary catheters 20a, 20b, 20c are mated to the end cap 34 to form a fluid-tight seal around the bores 36 in the end cap 34. A variety of mating techniques can be used to connect the end cap 34 to the connecting end 16 of the primary catheter 12. By way of non-limiting example, the end cap 34 can be welded, ultrasonically bonded, adhesively attached, or mechanically mated to the primary catheter 12.

Figure 3:
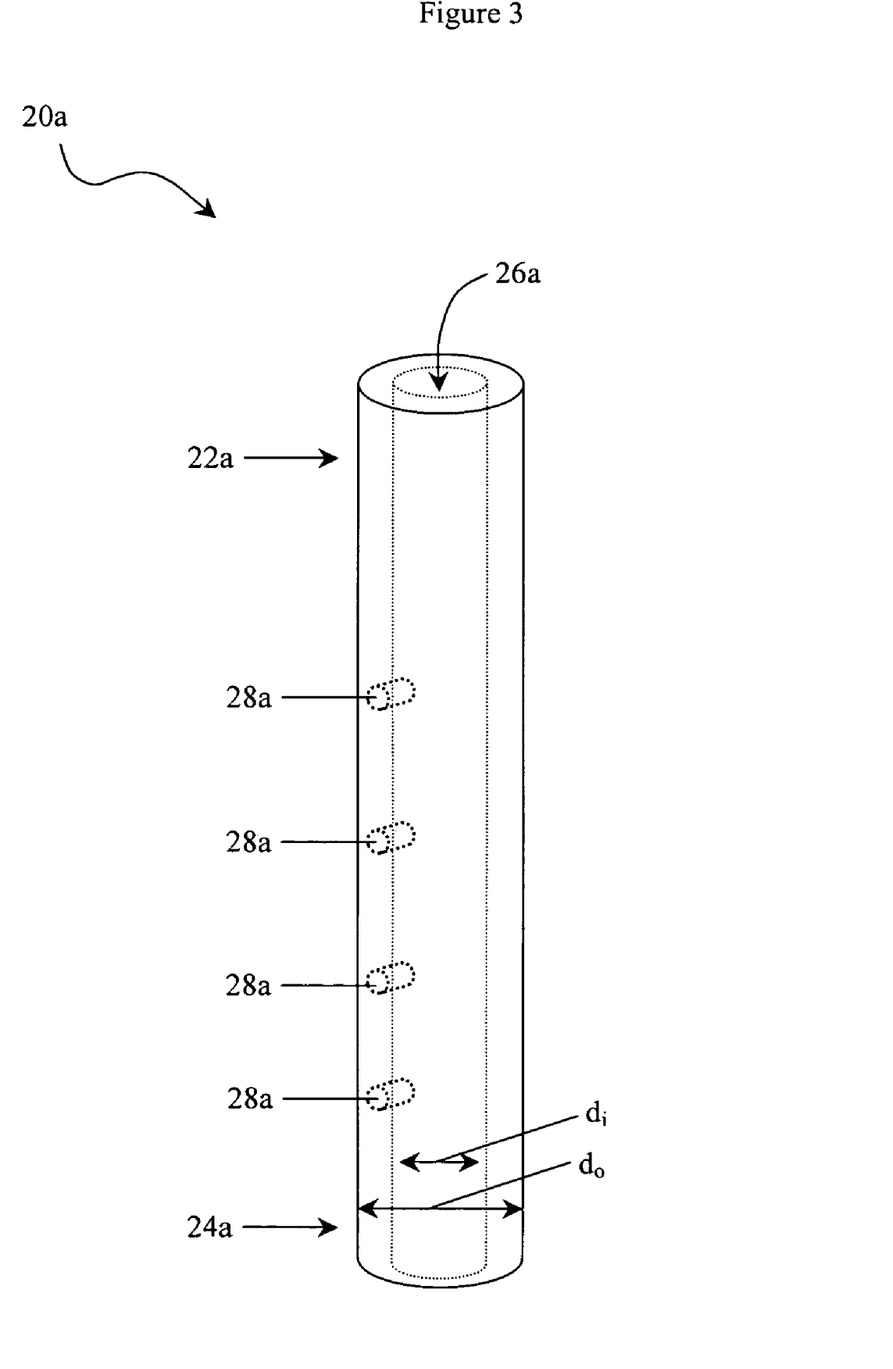
FIG. 3 is a perspective view of one of the secondary catheters shown in FIG. 2A.

The secondary catheters 20a, 20b, 20c each include at least one fluid entry port 28a, 28b, 28c formed therein so as to be in fluid communication with the fluid passageway 26a, 26b, 26c. FIG. 3 illustrates a single secondary catheter 20a having four fluid entry ports 28a. The size, shape, and position of the entry ports 28a can vary, but each entry port 28a should have a size and shape sufficient to allow fluid to flow therethrough and into or out of the fluid passageway 26a. The shape of each entry port 26a can be, for example, cylindrical, square, rectangular, etc. As shown in FIG. 3, the entry ports 28a each have a substantially cylindrical shape. The diameter of the entry ports 28a can also vary, but is preferably in the range of about 0.75 mm to 1.5 mm mm.

Referring back to FIG. 2A, while the position of the entry ports 28a can vary, the entry ports 28a are preferably disposed on an inwardly facing portion of each secondary catheter 20a, 20b, 20c, such that the entry ports 28a on catheter 20a face toward the entry ports 28b on catheter 20b, and the entry ports 28c (not shown) on catheter 20c. That is, the entry ports 28 should face inwardly and generally in the direction of a central longitudinal axis (L) of the shunt device. Moreover, the entry ports 28 are preferably spaced apart from each other, and are spaced apart from entry ports 28 on adjacent secondary catheters 20, as shown in FIG. 2A. A person having ordinary skill in the art will appreciate that the entry ports 28 can have virtually any size, shape, and position on the secondary catheters 20.

The size and shape of the secondary catheters 20 can vary, but each catheter preferably has an outer diameter $d_o$ in the range of about 1 mm to 1.5 mm, and an inner diameter $d_i$, which defines the size of the fluid passageway, in the range of about 0.5 mm to 0.8 mm, as shown in FIG. 3. The combined nominal outer diameter $d_n$ of all of the secondary catheters 20, as shown in FIG. 2C, is preferably substantially the same as, or less than, the diameter $d_p$ of the primary catheter 12, and more preferably is in the range of about 2 mm to 3 mm.

Figure 4A:
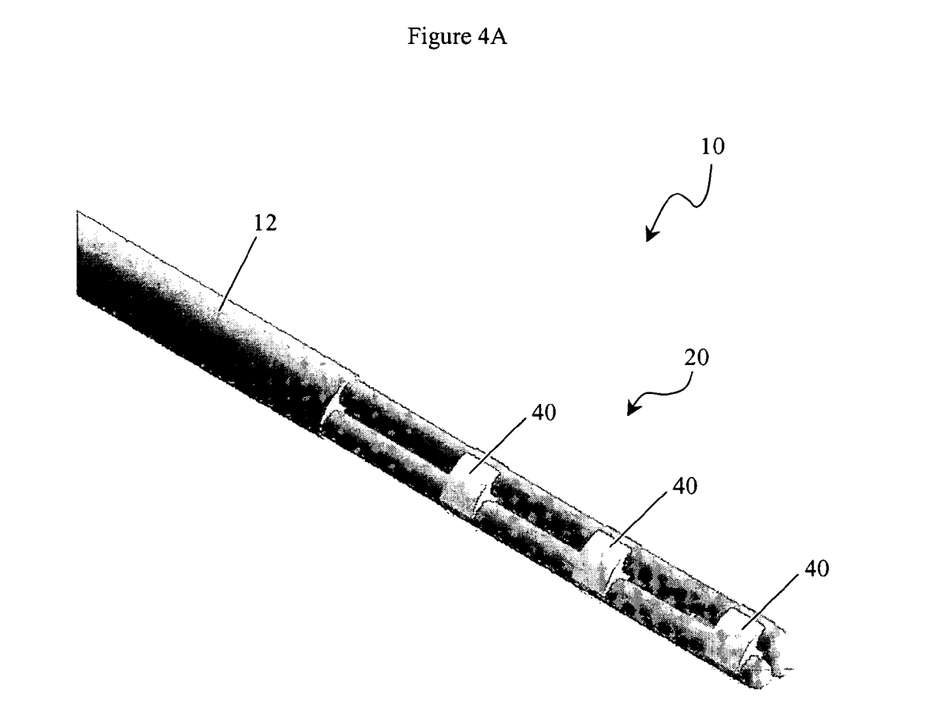
FIG. 4A is a perspective view of another embodiment of a shunt device having at least one support bracket disposed between several secondary catheters.

In another embodiment, shown in FIG. 4A, the shunt device 10 includes at least bracket 40, or spacing member, disposed between the secondary catheters for mating the catheters 20, and optionally for positioning the catheters at a predetermined distance apart from each other. The brackets 40 can have virtually any shape and size, but should be adapted to mate the secondary catheters 20 together to facilitate insertion of the shunt device 10 into a treatment site. The brackets 40 are particularly advantageous in that they prevent adhesion, or compression, of the secondary catheters 20a, 20b, 20c to each other during shipping, and also after the device 10 is implanted. This is particularly important since the fluid entry ports 28 are disposed on the inwardly facing portion of each secondary catheter 20.

Figure 4B:
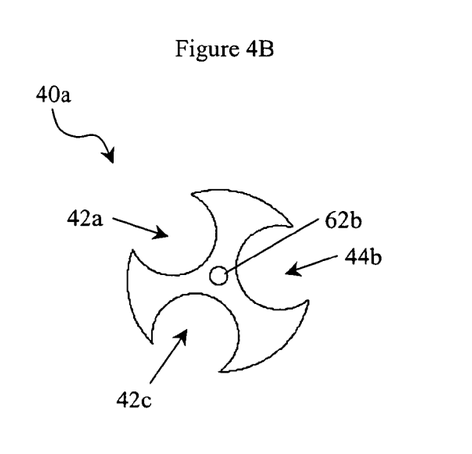
FIG. 4B is a plan view of one embodiment of a support bracket for use with a shunt device according to the present invention.
Figure 4C:
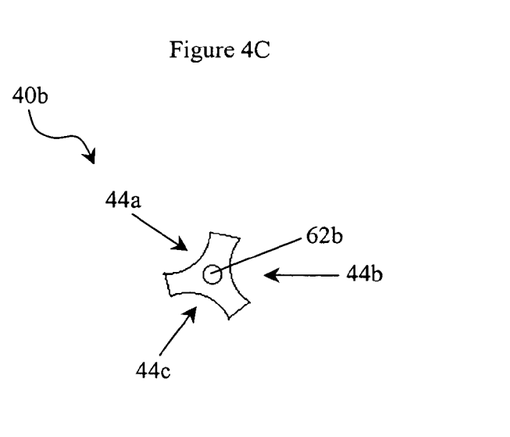
FIG. 4C is a plan view of another embodiment of a support bracket for use with a shunt device according to the present invention.

By way of non-limiting example, FIGS. 4B and 4C illustrate two embodiments of a bracket 40a, 40b for connecting, and optionally spacing apart, the secondary catheters 20. Bracket 40a, shown in FIG. 4B, has a generally circular shape with cut-out portions 42a, 42b, 42c which are sized to receive a secondary catheter 20. The cut-out portions 42a, 42b, 42c are preferably spaced apart to position the secondary catheters 20a, 20b, 20c at a predetermined distance apart from each other. This allows fluid to flow in between the catheters 20a, 20b, 20c and into or out of the fluid entry ports 28a, 28b, 28c. Preferably, the cut-out portions 42a, 42b, 42c are configured to separate the catheters 20a, 20b, 20c by a distance that is sufficient to allow fluid to flow therebetween, yet to prevent debris or tissue from entering into the space between the catheters 20a, 20b, 20c. In an exemplary embodiment, the space between the secondary catheters 20a, 20b, 20c is in the range of about 0.125 mm to 0.5 mm.

The bracket 40b shown in FIG. 4C is similar to the bracket 40a shown in FIG. 4B. However, rather than having cut-out portions 42a, 42b, 42c to receive the secondary catheters 20a, 20b, 20c, the bracket 40b has a substantially triangular shape that includes three concave portions 44a, 44b, 44c. Each secondary catheter 20a, 20b, 20c can be fixedly attached to a concave portion 44a, 44b, 44c.

The secondary catheters 20a, 20b, 20c can be mated to the brackets 40 using a variety of techniques. By way of non-limiting example, the secondary catheters 20a, 20b, 20c can mate to the brackets 40 using an interference fit, a sliding engagement, or any other type of mating technique. The secondary catheters 20a, 20b, 20c can optionally be fixedly attached to the brackets 40. For example, the secondary catheters 20a, 20b, 20c can be welded, ultrasonically bonded, adhesively attached, or mechanically mated to the brackets 40.

Figure 5:
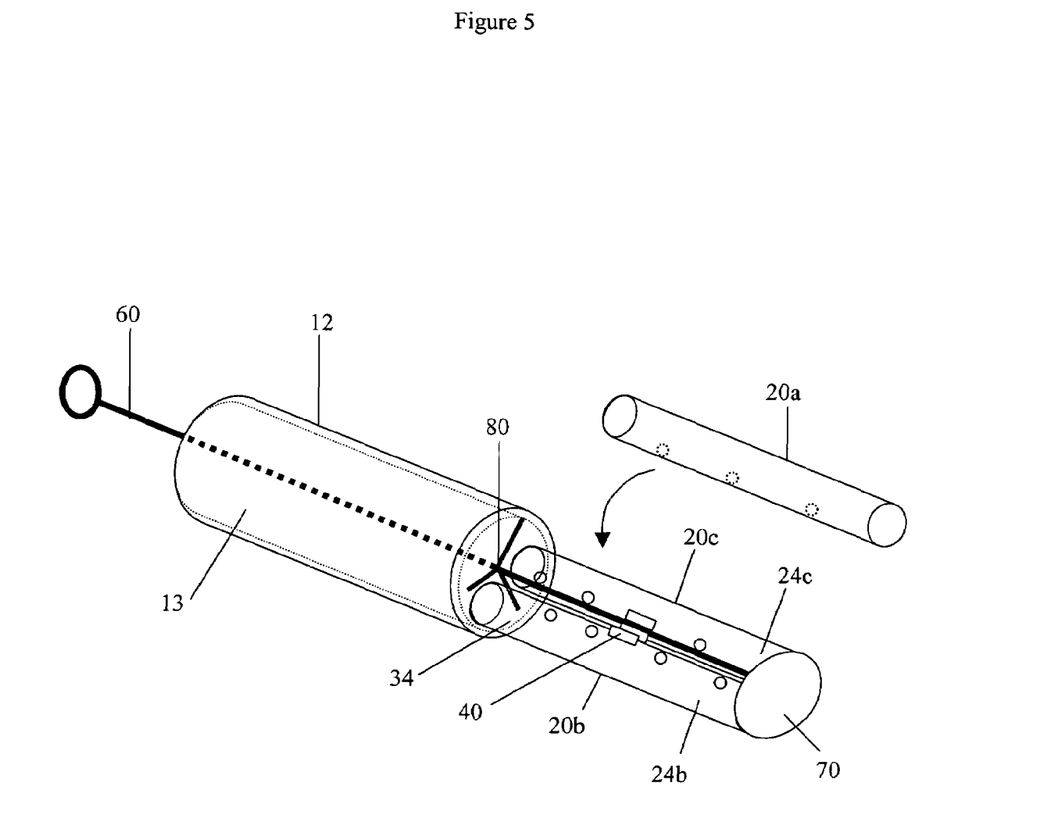
FIG. 5 is a perspective view of a partially assembled shunt device according to yet another embodiment of the present invention.

The shunt device 10 can also be adapted to receive an endoscope or rigid stylet 60, as shown in FIG. 5. For illustration purposes, secondary catheter 20a is shown detached from the device 10. The stylet 60 can be inserted through the inner lumen 13 and the fluid passageway 26a, 26b, 26c of one of the secondary catheters 20a, 20b, 20c. More preferably, however, the stylet 60 extends within the inner lumen 13 and through a self-sealing valve 80 formed in the end cap 34 of the primary catheter 12. The stylet then passes between the secondary catheters 20a, 20b, 20c. The self-sealing valve 80 can have a variety of configurations such as, for example, a slit formed in the end cap 34. The valve 80 could also be formed from a self-sealing elastomeric membrane or septum disposed across an opening formed in the center of the end cap 34. A person having ordinary skill in the art will appreciate that virtually any type of self-sealing valve can be provided for allowing the stylet 60 to be inserted through the end cap 34 without allowing fluid to flow through the valve.

The brackets 40 can also optionally include a central bore extending therethrough for slidably receive the rigid stylet 60.

FIGS. 4B and 4C each illustrate a bracket 40a, 40b having a central bore 62a, 62b extending therethrough.

In another embodiment, also shown in FIG. 5, the device 10 can include a distal cap 70 disposed around the distal ends 24a, 24b, 24c of the secondary catheters 20a, 20b, 20c. The distal cap 70 can have a variety of shapes and sizes, but preferably has rounded edges to prevent the device 10 from tearing or puncturing tissue while being implanted. As shown in FIG. 5, the distal cap 70 is a semi-spherical object that extends entirely around the distal tips 24a, 24b, 24c of the secondary catheters 20a, 20b, 20c. The distal cap 70 can also be effective to prevent the rigid stylet 60 from extending beyond the distal end of the device 10 when the stylet 60 is fully inserted into the device 10.

The distal cap 70 and brackets 40 are preferably made from a variety of biologically compatible materials. Suitable materials include, for example, titanium alloy, stainless steel, or tantalum. The distal cap 70 and brackets 40, 40a, 40b can optionally be formed from a bioabsorbable material, and/or a flexible, expanding material. Thus, once implanted, the end cap 70 and brackets 40 will eventually be absorbed into the body thereby allowing the secondary catheters 20a, 20b, 20c to separate. The primary and secondary catheters 12, 20 can also be made from a variety of biologically compatible materials. Preferably, the primary and secondary catheters 12, 20 are made from a flexible material such as, for example, a silicone elastomer.

In use, stylet 60 is inserted through the primary catheter 12, the self-sealing valve 80, between the secondary catheters 20a, 20b, 20c, and through the brackets 40. The stylet 60 is effective to provide rigidity to the device for facilitating insertion of the device into a treatment site. Once the device 10 is implanted at the treatment site, the stylet 60 can be removed. The CSF is free to flow between the secondary catheters 20a, 20b, 20c and into the fluid entry ports 28a, 28b, 28c. The CSF then flows through the fluid passageway 28a, 28b, 28c, into the inner lumen 13 of the primary catheter 12, and to the open end 14 of the primary catheter where the CSF is deposited at a site in the body where it can be absorbed into the patient's circulatory system.

A person having ordinary skill in the art will appreciate that while the invention is described in connection with the use of a rigid stylet, an endoscope can additionally, or alternatively be used for visualizing the surgical site during implantation of the catheter. The endoscope can optionally provided rigidity to the catheter in place of the rigid stylet. In other embodiments, the bracket 40 optionally be formed from a flexible, expanding material to allow the catheter to be used with stylets, endoscopes, or other devices having varying outer diameters.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable catheter, comprising:
   an elongate trunk conduit having a first end, a second end, and an outer wall that defines an inner lumen; and
   a plurality of branch conduits coupled to one another and extending from the second end of the elongate trunk conduit, each branch conduit including an inner lumen in fluid communication with the inner lumen of the elongate trunk conduit, and at least one port extending into the inner lumen of the branch conduit;

wherein the catheter is configured to removably receive a rigid stylet through the inner lumen of the elongate trunk and between the plurality of branch conduits, and wherein a distal end of the plurality of branch conduits are connected by an end cap that is adapted to seat a distal end of the rigid stylet; and wherein the second end of the elongate trunk conduit includes a self-sealing valve adapted to receive a rigid stylet therethrough, the self-sealing valve being in fluid communication with the inner lumen and in direct fluid communication with an external environment surrounding the catheter.

2. The implantable catheter of claim 1, wherein each of the plurality of branch conduits has a generally elongate cylindrical shape and includes an open proximal end mated to the elongate trunk conduit, and a closed distal end.

3. The implantable catheter of claim 1, wherein the plurality of branch conduits are radially positioned at a distance apart from one another, and wherein the at least one port is disposed on an inwardly facing portion of each of the branch conduits.

4. The implantable catheter of claim 3, further comprising at least one connector bracket disposed between each of the plurality of branch conduits and adapted to maintain the branch conduits at a distance apart from each other.

5. The implantable catheter of claim 4, wherein the at least one connector bracket includes a central port formed therethrough for receiving a rigid stylet.

6. The implantable catheter of claim 1, wherein the elongate trunk conduit and the plurality of branch conduits are formed from a flexible material.

7. The implantable catheter of claim 1, wherein the catheter includes three branch conduits.

8. An implantable catheter, comprising:
an elongate trunk conduit having a first end, a second end, and an outer wall that defines an inner lumen;
a plurality of branch conduits coupled to one another and extending from the second end of the elongate trunk conduit, each branch conduit including an inner lumen in fluid communication with the inner lumen of the elongate trunk conduit, and at least one port extending into the inner lumen of the branch conduit;

wherein the plurality of branch conduits have a combined nominal outer diameter that is substantially the same or less than a maximum outer diameter of the elongate trunk conduit; and at least one connector bracket disposed between each of the plurality of branch conduits and adapted to maintain the branch conduits at a distance apart from each other.

9. The implantable catheter of claim 8, wherein a distal end of the plurality of branch conduits are connected by an end cap that is adapted to seat a distal end of the rigid stylet such that it prevents the rigid stylet from extending beyond the distal end of the plurality of branch conduits.

10. An implantable catheter, comprising:
an elongate trunk conduit having a first end, a second end, and an outer wall that defines an inner lumen; and
a plurality of branch conduits coupled to one another and extending from the second end of the elongate trunk conduit, each branch conduit including an inner lumen in fluid communication with the inner lumen of the elongate trunk conduit, and at least one port extending into the inner lumen of the branch conduit;

wherein the catheter is configured to removably receive a rigid stylet through the inner lumen of the elongate trunk and between the plurality of branch conduits, and wherein a distal end of the plurality of branch conduits are connected by an end cap that is configured to seat a distal end of the rigid stylet such that it prevents the rigid stylet from extending beyond the distal end of the plurality of branch conduits.

11. The implantable catheter of claim 10, further comprising at least one connector bracket disposed between each of the plurality of branch conduits and adapted to maintain the branch conduits at a distance apart from each other.

12. The implantable catheter of claim 11, wherein the at least one connector bracket includes a central port formed therethrough for receiving a rigid stylet.

\* \* \* \* \*